United States Patent
Chen et al.

[19]

[11] Patent Number: 5,955,465

[45] Date of Patent: *Sep. 21, 1999

[54] 1,2,4-TRIAZOLO[4,3-C]QUINAZOLIN-3-ONES AND 1,2,4-TRIAZOLO[4,3-C]QUINAZOLIN-3-THIONES

[75] Inventors: Paul Chen, North Branford; Alan Hutchison, Madison, both of Conn.

[73] Assignee: Neurogen Corporation, Branford, Conn.

[ * ] Notice: This patent is subject to a terminal disclaimer.

[21] Appl. No.: 08/946,040

[22] Filed: Oct. 7, 1997

Related U.S. Application Data

[63] Continuation of application No. 08/621,000, Mar. 22, 1996, Pat. No. 5,677,309.

[51] Int. Cl.[6] .................. A01N 43/54; C07D 257/08; C07D 487/00; C07D 239/00

[52] U.S. Cl. .................. 514/267; 544/179; 544/184; 544/251

[58] Field of Search .................. 544/251, 179, 544/184; 514/267

[56] References Cited

U.S. PATENT DOCUMENTS

| | | | |
|---|---|---|---|
| 4,312,870 | 1/1982 | Yokoyama | 424/258 |
| 4,713,383 | 12/1987 | Francis et al. | 514/267 |
| 5,173,492 | 12/1992 | Suzuki et al. | 514/267 |
| 5,677,309 | 10/1997 | Chen et al. | 514/267 |

FOREIGN PATENT DOCUMENTS

| | | |
|---|---|---|
| 0 181 282 A1 | 5/1986 | European Pat. Off. |
| 0 217 748 A2 | 4/1987 | European Pat. Off. |
| 0 263 071 A1 | 4/1988 | European Pat. Off. |
| WO 93 17025 | 9/1993 | WIPO . |
| 9532205 | 11/1995 | WIPO . |

*Primary Examiner*—Richard L. Raymond
*Assistant Examiner*—Tamthom N. Truong
*Attorney, Agent, or Firm*—McDonnell Boehnen Hulbert & Berghoff

[57] ABSTRACT

The present invention encompasses structures of the Formula:

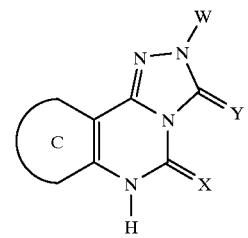

or the pharmaceutically acceptable non-toxic salts thereof wherein:

X is oxygen, $H_2$, or sulfur;

Y is oxygen or sulfur;

W is alkyl, arylalkyl, or heteroarylalkyl, each of which is optionally substituted; or W is aryl or heteroaryl;

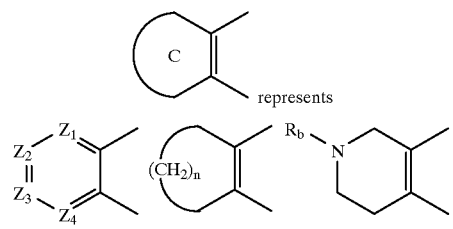

wherein:

$Z_1$, $Z_2$, $Z_3$, and $Z_4$ independently represent nitrogen or C—$R_a$, where
each $R_a$ independently is hydrogen, an inorganic substitutent or an optionally substituted aromatic group;

n is 1, 2 or 3; and $R_b$ is hydrogen, alkyl, or an optionally substituted aromatic group,
which compounds are highly selective agonists, antagonists or inverse agonists for GABAa brain receptors or prodrugs thereof and are useful in the diagnosis and treatment of anxiety, sleep, and seizure disorders, overdose with benzodiazepine drugs, and enhancement of memory.

12 Claims, No Drawings

1,2,4-TRIAZOLO[4,3-C]QUINAZOLIN-3-ONES AND 1,2,4-TRIAZOLO[4,3-C]QUINAZOLIN-3-THIONES

This is a continuation of application Ser. No. 08/621,000 filed Mar. 22, 1996 now U.S. Pat. No. 5,677,309.

BACKGROUND OF THE INVENTION

1. Field of the Invention

This invention relates to 1,2,4-triazolo[4,3-c]quinazolin-3-ones and 1,2,4-triazolo[4,3-c]quinazolin-3-thiones which selectively bind to GABAa receptors. This invention also relates to pharmaceutical compositions comprising such compounds. It further relates to the use of such compounds in treating anxiety, sleep and seizure disorders, overdoses of benzodiazepine-type drugs, and enhancing alertness.

2. Description of the Related Art

γ-Aminobutyric acid (GABA) is regarded as one of the major inhibitory amino acid transmitters in the mammalian brain. Over 30 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmnakol. 258: 69–82). All subsequent electrophysiological studies (reviewed in Tallman et al. 1980, Science 207:274–81, Haefley et al., 1981, Handb. Exptl. Pharmacol. 33: 95–102) have generally confirmed this funding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 249–60, Mohler & Okada, 1977, Science 198: 854–51, Mohler & Okada, 1977, Br. J. Psychiatry 133: 261–68). The average therapeutic doses of these drugs in man also correlate with receptor potency (Tallman et al. 1980, Science 207: 274–281).

In 1978, it became clear that GABA and related analogs could interact at the low affinity (1 mM) GABA binding site to enhance the binding of benzodiazepines to the clonazepamsensitive site (Tallman et al. 1978, Nature, 274: 383–85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (–) bicucumine is much less active (Tallman et al., 1978, Nature, 274: 383–85).

Soon after the discovery of high affinity binding sites for the benzodiazepines, it was discovered that a 1,2,4-triazolo [4,3-b]pyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, 1,2,4-trazolo[4,3-b]pyridazine interacted with benzodiazepine sites with a Hill coefficient of 1 (Squires et al., 1979, Pharma. Biochem. Behav. 10: 825–30, Klepner et al. 1979, Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212: 337–46, Young et al., 1981 J. Pharmacol Exp. ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites has been demonstrated by Sieghart & Karobath, 1980, Nature 286: 285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor tppes. The major labeled bands have molecular weights of 50,000 to 53,000, 55,000, and 57,000 and the 1,2,4-triazolo[4,3-b]pyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into , β, γ, δ, and ε, and provide a molecular basis for the GABAa receptor heterogeneity and distinctive regional pharmacology (Shivvers et al., 1980; Levitan et al., 1989). The g subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predictive for the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen & Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazo[1,5-a][1,4] benzodiazepine(Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. J. Clin. Pharmacol. 14: 569–70). When a radiolabeled form of this compound was studied (Mohler & Richards, 1981, Nature 294: 763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blockdng both types of activity have been termed antagonists. This categorization has been developed to emphasize the fact that a wide variety of compounds can produce a spectrum of phamnacologica effects, to indicate that compounds can interact at the same receptor to produce opposite effects, and to indicate that beta-carbolines and antagonists with intrinsic anxiogenic effects are not synonymous.

A biochemical test for the pharmacological and behavioral properties of compounds that interact with the benzodiazepine receptor continues to emphasize the interaction with the GABAergic system In contrast to the benzodiazepines, which show an increase in their affinity due to GABA (Talman et al., 1978, Nature 274: 383–85, Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA (Braestrup & Nielson 1981, Nature 294: 472–474). Thus, the GABA shift predicts generally the expected behavioral properties of the compounds.

Various compounds have been prepared as benzodiazepine agonists and antagonists. For example, U.S. Pat. Nos. 4,312,870 and 4,713,383, and European Patent Application EP 181,282 disclose assorted compounds useful in treating anxiety or depression. U.S. Pat. No. 4,713,383 teaches compounds of the formula:

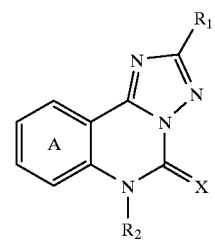

wherein $R_1$=(un)substituted phenyl, (dihydro)furanyl, tetrahydrofuranyl, (dihydro)thienyl, tetrahydrothienyl, pyranyl, ribofuranosyl, all C-attached; $R_2$=hydrogen, alkyl; X=O, S, $R_3N$; $R_3$=hydrogen, alkenyl, alkynyl, $C_{3-20}$ cycloalkyl, (un)substituted alkyl, aryl, aralkyl, where aryl is phenyl, pyridinyl, thienyl, furanyl; ring A may be substituted by alkyl, alkoxy, halo, amino, alkylthio, etc.

European Patent Application EP 181,282 discloses compounds of the formula:

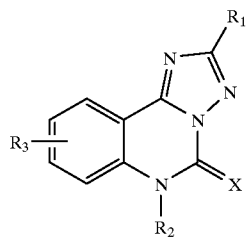

wherein R₁=(substituted) phenyl or heterocycle; R₂=hydrogen, alkyl, alkenyl, hydroxyalkyl, aralkyl, aralkenyl, aryl; R₃=hydrogen, alkyl, alkoxy, hydroxy, halo, trifluoromethyl, nitro, amino, alkylthio, alkylsulfinyl, alkylsulfonyl, aralkoxy; X=O, S, NR₄; and R₄=hydrogen, alkyl, aralkyl, cycloalkyl, alkenyl, alkynyl, aryl, (substituted) aminoaklyl, hydroxyalkyl.

U.S. Pat. No. 4,312,870 teaches compounds of formulas:

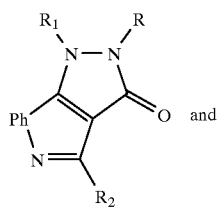 and

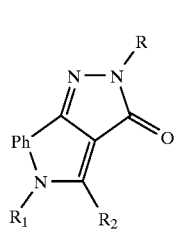

where

Ph is 1,2-phenylene, unsubstituted or substituted by up to 3 identical or different members selected from lower alkyl, lower alkoxy, lower alkylthio, hydroxy, halogen, trifluoromethyl, nitro, amino, mono- or di-lower alkylamino, cyano, carbamoyl and carboxy; R is unsubstituted or substituted phenyl as defined by phenyl, pyridyl, lower alkylpyridyl, or halogenopyridyl; R₁ is hydrogen, lower alkyl or hydroxyloweralkyl or lower dialkylamino or phenylalkyl; and R₂ is hydrogen or lower alkyl alkyl; their 3-hydroxy-tautomers; lower alkanoyl, carbamoyl, mono- or di-lower alkyl-carbamoyl derivatives of said (hydroxy or amino)-(phenyl or phenylene) compounds;

and

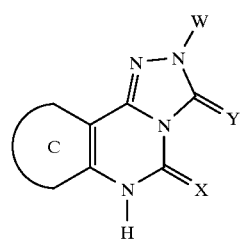

where

R" is hydrogen, alkyl or alkoxy with up to 4 carbon atoms each, hydroxy, fluoro, chloro, bromo, or trifluoromethyl; and R' is hydrogen, o- or m-fluoro; or it is p-fluoro when R" is chloro.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in enhancing alertness, treatment of seizure, anxiety, and sleep disorders, and treatment of benzodiazepine overdoses. Accordingly, a broad embodiment of the invention is directed to compounds of Formula I:

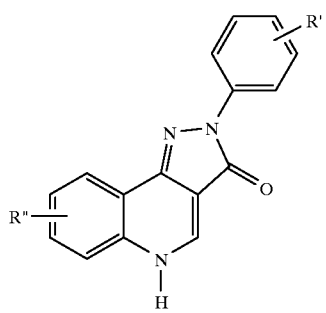

or the pharmaceutically acceptable non-toxic salts thereof wherein:

X is oxygen, H₂, or sulfur,

Y is oxygen or sulfur,

W is alkyl, arylalkyl, or heteroarylalkyl, each of which is optionally substituted with up to two groups selected from halogen, alkyl, alkoxy, trifluoromethyl, aminoalkyl, or mono- or dialkylamino; or W is aryl, heterocyclyl containing 1–4 heteroatoms, or heteroaryl containing 1–4 heteroatoms, each of which is optionally substituted with up to two groups selected from halogen, hydroxy, hydroxyalkyl, alkyl, lower alkoxy, amino optionally substituted with up to two alkyl groups, aminoalkyl where the amino portion is optionally substituted with up to two alkyl groups; alkylaminocarbonylalkyl where the amino portion is optionally substituted with alkyl; or alkoxyalkyl;

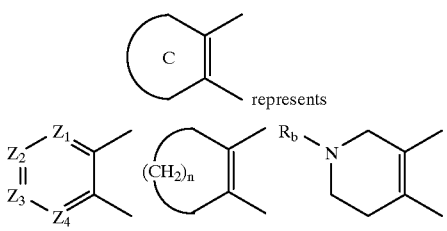

wherein:
  $Z_1$, $Z_2$, $Z_3$, and $Z_4$ independently represent nitrogen or C-$R_a$, where
    each $R_a$ independently is hydrogen, halogen, hydroxy, amino, or phenyl or pyridyl where phenyl and pyridyl are optionally substituted with halogen, alkyl, or alkoxy;
  n is 1, 2 or 3; and
  $R_b$ is hydrogen, alkyl, phenyl, 2-, 3- or 4-pyridyl, phenylalkyl, or 2-, 3-, or 4-pyridylalkyl, where each phenyl or pyridyl ring is optionally substituted with up to two groups selected from halogen, hydroxy, alkyl, or alkoxy.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep, and seizure disorders, overdose with benzodiazepine drugs, and enhancement of memory.

DETAILED DESCRIPTION OF THE INVENTION

As used herein, the term "aryl" refers to aromatic carbocyclic groups having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), each of which can optionally be substituted with e.g., halogen, lower alkyl, lower alkylthio, trifluoromethyl, lower acyloxy, aryl, and heteroaryl.

A preferred aryl group is phenyl optionally substituted with up to five groups selected independently from halogen, cyano, hydroxy, straight or branched chain lower alkyl having 1–6 carbon atoms or cycloalkyl having 3–7 carbon atoms, amino, mono or dialkylamino where each alkyl is independently straight or branched chain lower alkyl having 1–6 carbon atoms or cycloalkyl having 3–7 carbon atoms, straight or branched chain lower alkoxy having 1–6 carbon atoms, cycloalkyl alkoxy having 3–7 carbon atoms, or $NR_1COR_2$, $COR_2$, $CONR_1R_2$ or $CO_2R_2$ where $R_1$ and $R_2$ are the same or different and represent hydrogen or straight or branched chain lower alkyl having 1–6 carbon atoms or cycloalkyl having 3–7 carbon atoms By heteroaryl is meant aromatic ring systems having at least one and up to four hetero atoms selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, napthyridinyl, isoxazolyl, phthalazinyl, furanyl, quinolinyl, isoquinolinyl, thiazolyl, and thienyl, each of which can optionally be substituted with, e.g., halogen, lower alkyl, lower alkoxy, lower alkylthio, trifluoromethyl, lower acyloxy, aryl, heteroryl, and hydroxy.

The aryl and heteroaryl groups herein are systems characterized by 4n+2 π electrons, where n is an integer.

In addition to those mentioned above, other examples of the aryl and heteroaryl groups encompassed within the invention are the following:

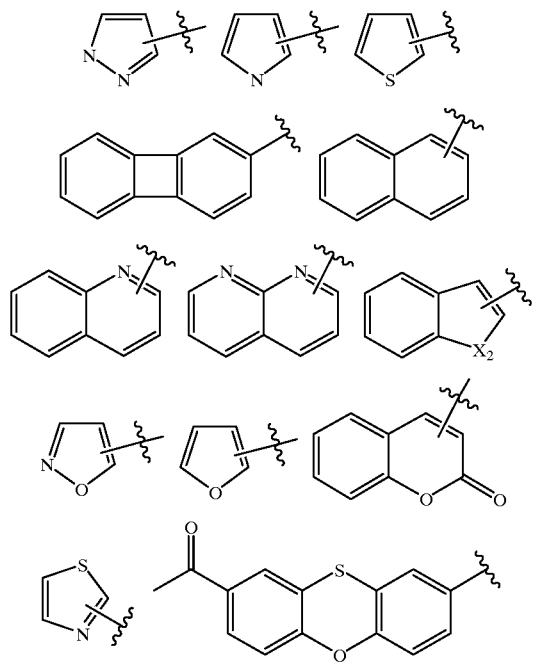

As noted above, each of these groups can optionally be mono- or polysubstituted with groups selected independently from, for example, halogen, lower alkyl, lower alkoxy, lower alkylthio, trifluoromethyl, lower acyloxy, aryl, heteroaryl, and hydroxy.

By "alkyl" and "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Unless indicated otherwise, the alkyl group substituents herein are optionally substituted with at least one group independently selected from hydroxy, mono- or dialkyl amino, phenyl or pyridyl.

By "alkoxy" and "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentoxy, isopentoxy, neopentoxy, hexoxy, 2-hexoxy, 3-hexoxy, and 3-methylpentoxy.

Still other examples of various aryl and heteroaryl groups are shown in Chart D of published International Application WO 93/17025.

By the term "halogen" or "Hal" in the present invention is meant fluorine, bromine, chlorine, and iodine.

In addition to compounds of general Formula I described above, the invention encompasses compounds of general Formula IA:

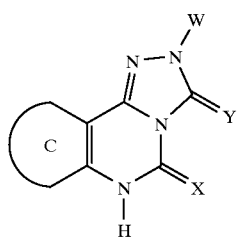

IA or the pharmaceutically acceptable non-toxic salts thereof wherein:

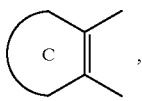

X and Y are as defined above for Formula I; and

W is alkyl, arylalkyl, or heteroarylalkyl, each of which is optionally substituted with up to two groups selected from halogen, alkyl, alkoxy, trifluoromethyl, aminoalkyl, or mono- or dialkylamino; or W is aryl, heterocyclyl containing 1–4 heteroatoms, or heteroaryl containing 1–4 heteroatoms, each of which is optionally substituted with up to two groups selected from halogen, hydroxy, hydroxyalkyl, alkyl, lower alkoxy, amino optionally substituted with up to two alkyl groups, aminoalkyl where the amino portion is optionally substituted with up to two alkyl groups; alkylaminocarbonylalkyl where the amino portion is optionally substituted with alkyl; or alkoxyalkyl.

In addition, the present invention encompasses compounds of Formula II.

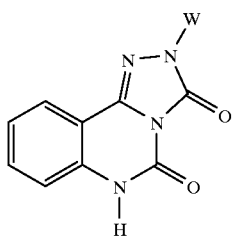

II wherein W is as defined above for Formula I.

Preferred compounds of Formula II are those where W represents phenyl substituted with a hydroxyalkyl group, preferably a hydroxy methyl group. Particularly preferred compounds of Formula II are those where W represents phenyl substituted in the para position, i.e. the 4 position with respect to the point of attachment to the triazoloquinazoline ring system, with a hydroxyalkyl group, preferably a hydroxy methyl group.

The present invention also encompasses compounds of Formula III:

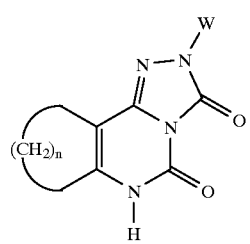

III wherein W is as defined above for Formula I.

Preferred compounds of Formula III are those where W represents phenyl mono or disubstituted with halogen, hydroxyalkyl, or alkylaminoalkyl. More preferred compounds of Formula III are those where W represents phenyl disubstituted with halogen, or phenyl monosubstituted with hydroxyalkyl, or alkylarninoalkyl. Other more preferred compounds of Formula III are those where W represents phenyl ortho and para substituted with fluoro, or phenyl para substituted with hydroxymethyl or methylaminomethyl The present invention also encompasses compounds of Formula IV:

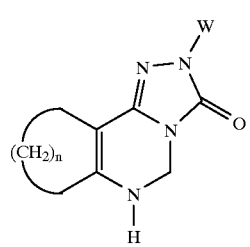

IV wherein

W is as defined above for Formula I; and n is 1, 2, or 3.

The present invention also encompasses compounds of Formula V:

V

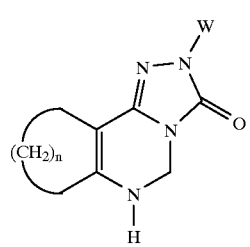

wherein

W is as defined above for Fornula I; and.

n is 1, 2, or 3.

The present invention also encompasses compounds of Fornula VI:

VI wherein W is as defined above for Formula I.

The present invention also encompasses compounds of Formula VII:

VII wherein W is as defined above for Formula I.

The present invention also encompasses compounds of Formula VIII:

VIII wherein
  W is as defined above for Formula I; and
  n is 1, 2, or 3.

The present invention also encompasses compounds of Formula IX:

IX wherein
  W is as defined above for Formula I; and
  n is 1, 2, or 3.

The present invention also encompasses compounds of Formula X:

X wherein W is as defined above for Formula I.

The invention further provides compounds of Formula XI, i.e., intermediates useful in the preparation of compounds of Formulas I–X:

XI where W is as defined above for Formula I and Hal represents a halogen

The invention also encompasses compounds of Formula XII, i.e., intermediates useful in the preparation of compounds of Formulas I–X:

XII where W is as defined above for Formula I and Hal represents a halogen.

The invention also encompasses intermediates of Formula XIII:

XIII where W is as defined above for Formula I and Hal represents a halogen.

Additional intermediates according to the invention are represented by Formula XIV:

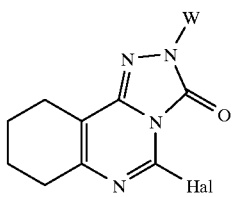

XIV where W is as defined above for Formula I and Hal represents a halogen.

Preferred compounds of the invention include W groups selected from the following:

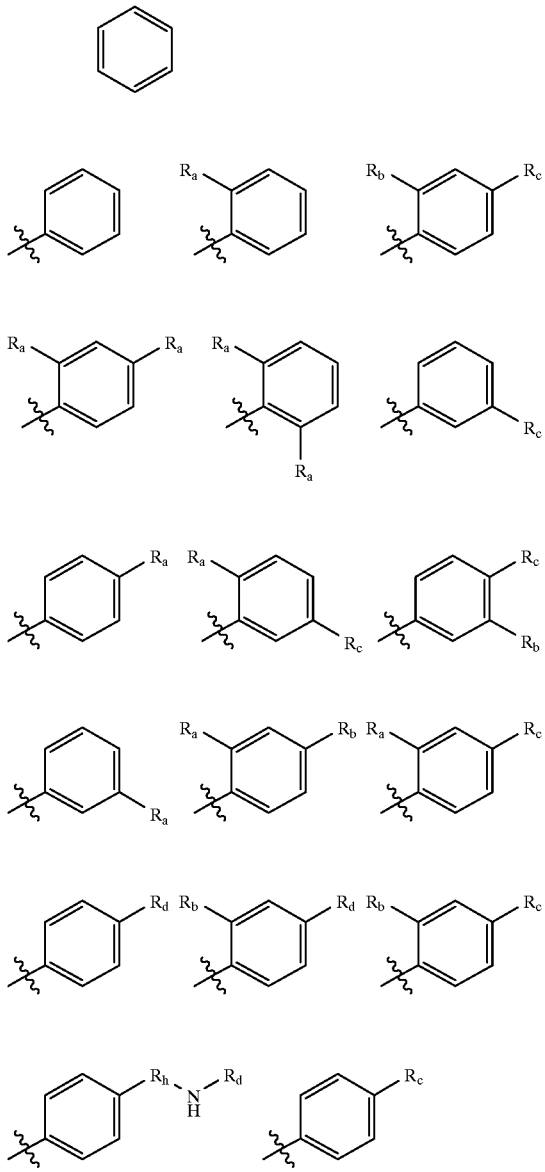

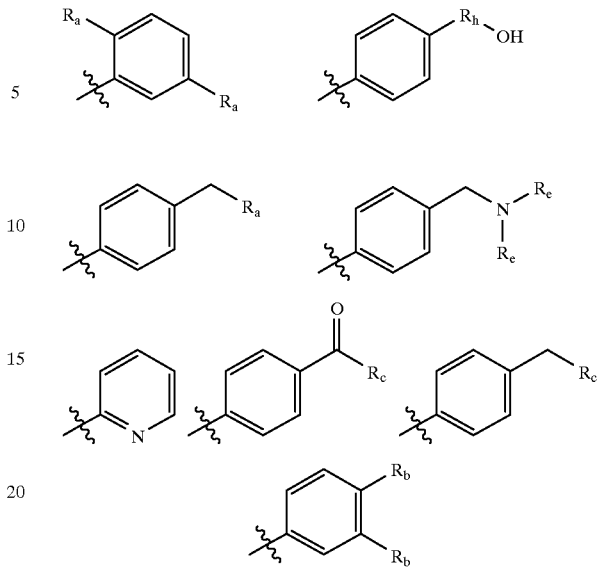

In the above W groups, the following definitions apply:

$R_a$ is halogen;

$R_b$ is hydroxy;

$R_c$ represents alkoxy, $R_d$ represents alkyl;

$R_e$ represents hydrogen or $R_d$;

$R_f$ represents hydrogen, or $R_c$;

$R_g$ represents hydrogen, $R_a$ or $R_c$; and $R_h$ represents alkylene of 1–6 carbon atoms.

In those formulas where more than one of the same substituent appears, those substituents are the same or different.

More preferred compounds of the invention include W groups selected from the following: 4(hydroxymethyl)phenyl; 2,4-difluorophenyl; and 4-(methylaminoethyl)phenyl.

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Representative compounds according to the invention are shown in Table 1 below.

TABLE 1
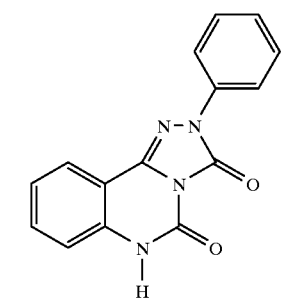
Compound 1
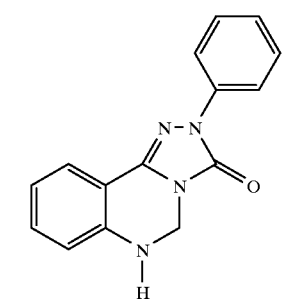
Compound 2
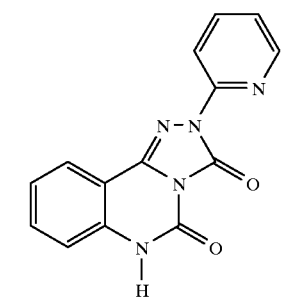
Compound 5
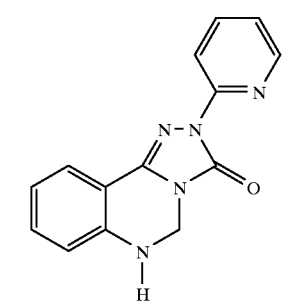
Compound 13
TABLE 1-continued
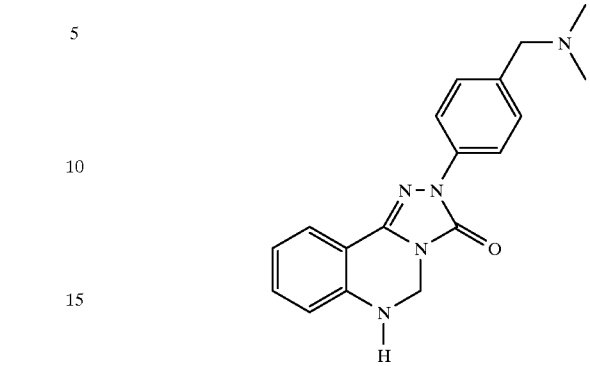
Compound 21
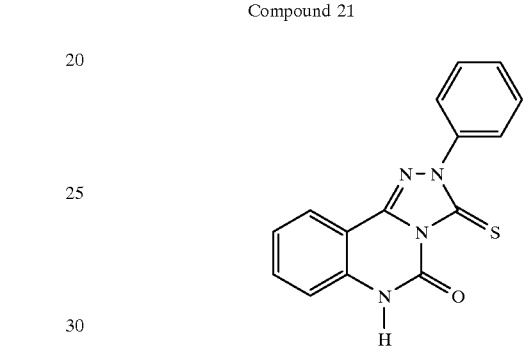
Compound 28
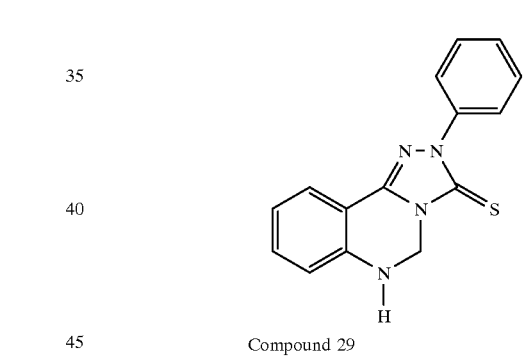
Compound 29
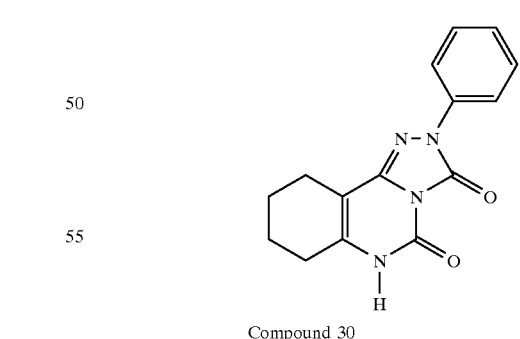
Compound 30

TABLE 1-continued

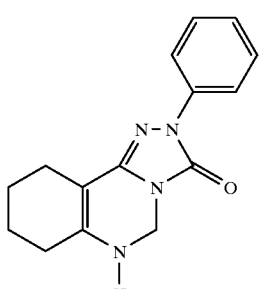

Compound 31

The pharmaceutical utility of compounds of this invention are indicated by the following assay for GABAa receptor activity. The interaction of 1,2,4-triazolo[4,3-c]quinazolin-3-ones and 1,2,4-triazolo[4,3-c]quinazolin-3-thiones of the invention with a GABA binding site, the benzodiazepines (BDZ) receptor, results in the pharmacological activities of these compounds.

Assays are carried out as described in Thomas and Tallman (J. Bio. Chem. 156: 9838–9842, J. Neurosci. 3: 433–440, 1983). Rat cortical tissue is dissected and homogenized in 25 volumes (w/v) of 0.05 M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05 M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated Total Specific Binding=Total−Nonspecific. In some cases, the amounts of unlabeled drugs is varied and total displacement curves of binding are carried out. Data are converted to Ki's; results for compounds of this invention are listed in Table 2.

TABLE 2

| Compound Number[1] | Ki(nM) |
|---|---|
| 1 | 5.9 |
| 2 | 12 |
| 5 | 7.6 |
| 13 | 63 |
| 21 | 53 |
| 28 | 4.5 |
| 29 | 636 |
| 30 | 4.5 |
| 31 | 8 |

[1]Compound numbers relate to compounds shown in Table 1.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and prserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil inediur, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Representative illustrations of the preparation of compounds of the present invention are given in Schemes I, II and III. Those having skill in the art will recognize that the starting materials may be varied and additional steps employed to produce compounds encompassed by the present invention, as demonstrated by the following examples.

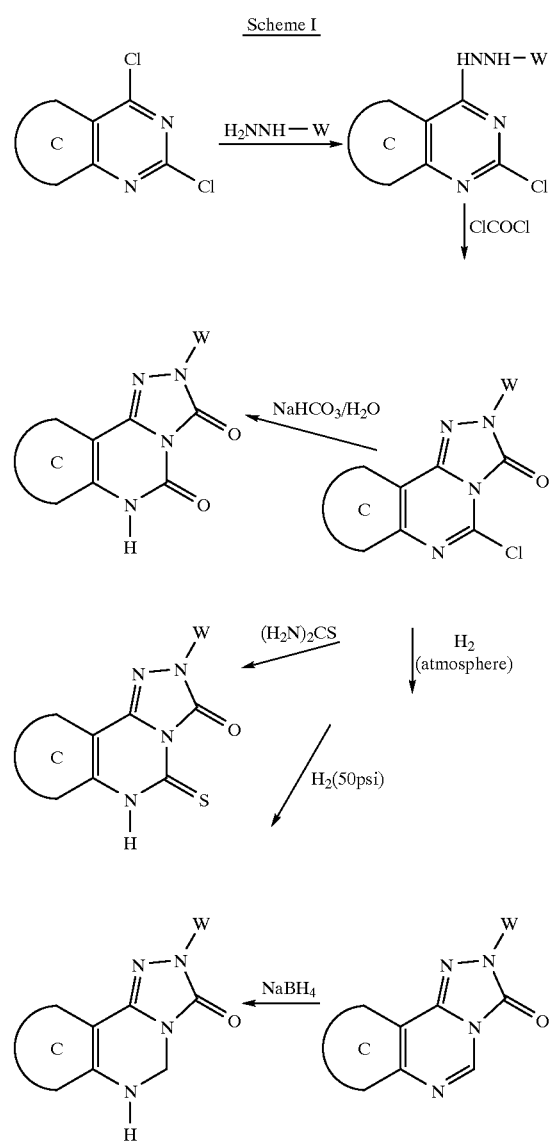

Scheme I

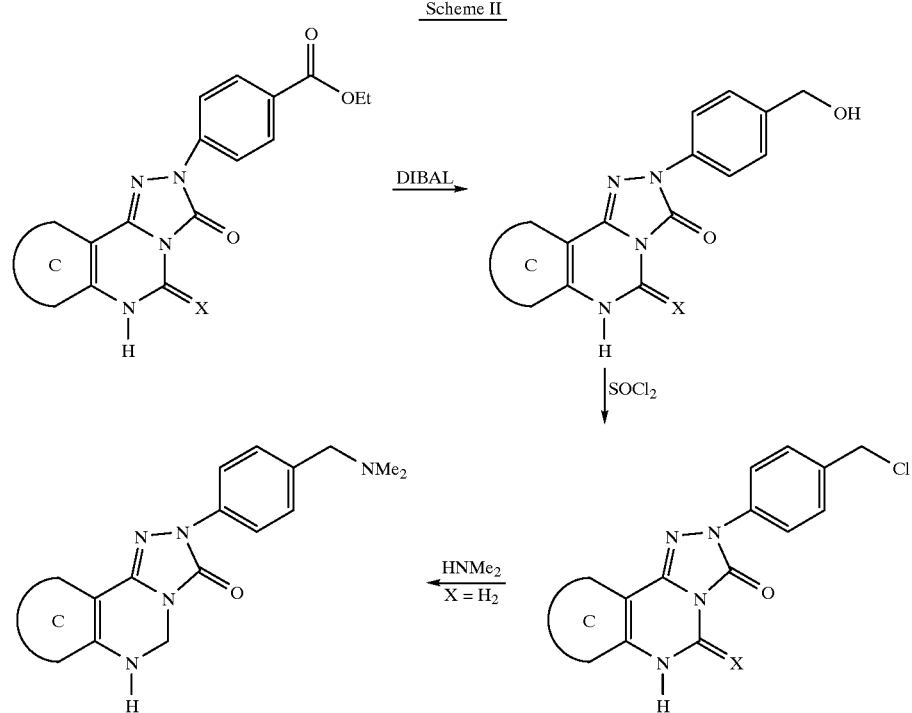
Scheme II
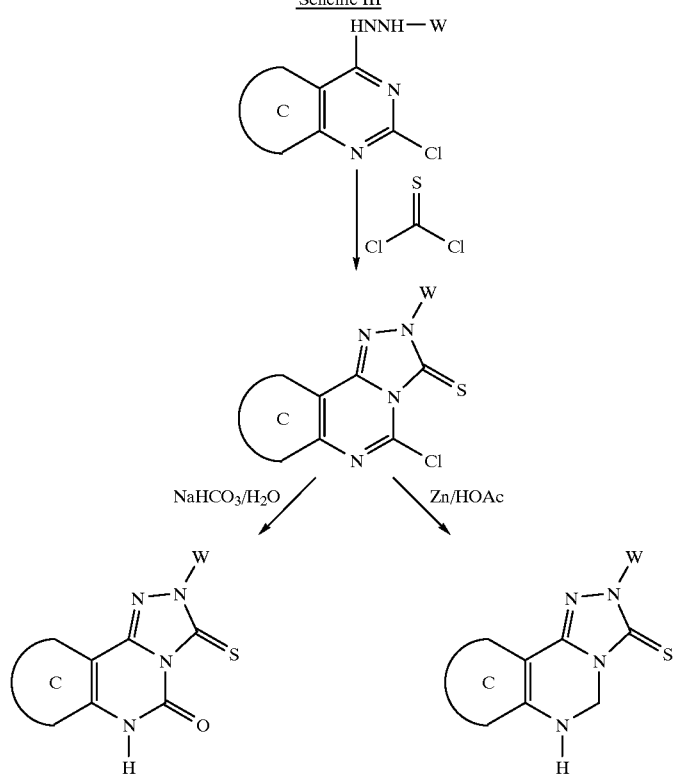
Scheme III

In Schemes I–III,

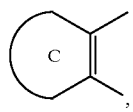

X, and W are as defined above for Formula I, except as noted otherwise in the schemes.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The disclosures in this application of all articles and references, including patents, are incorporated herein by reference in their entirety.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative methods for preparing intermediates of the invention are set forth below in the examples.

EXAMPLE I

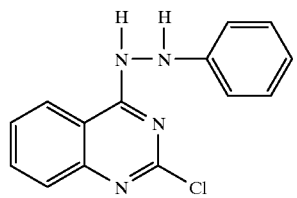

To a stirred solution of N,N-diisopropylethylamine (10 ml, 57 mmol) in THF (150 ml), 2,4dichloroquinazoline [prepared according to the procedure described by Curd, F. H. S. et al., J. Chem. Soc., (1947), 775] (5 g, 25 mmol) and phenylhydrazine (2.7 g, 25 mmol) was added. After stirring for 30 minutes, the reaction was poured into water and extracted with dichloromethane (3×100 ml). The combined organic layers were dried over $Na_2SO_4$ and evaporated under reduced pressure. The resulting solid was triturated with ethanol and filtered to afford 2-chloro-4-phenylhydrazinoquinazoline (3.2 g) as a yellow solid, m.p. 178° C. (dec.).

EXAMPLE II

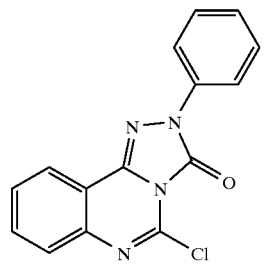

To a mixture of 2-chloro-4-phenylhydrazinoquinazoline (2 g, 7.4 mmol) and N,N-diisopropylethylamine (2 ml, 11.4 mmol) in THF was added phosgene (6 ml, 20% in Toluene) slowly, then stirred for additional 5 min. The reaction mixture was poured into water and extracted with ethyl acetate (2×100 ml). The combined organic layers were washed with brine and dried over $Na_2SO_4$ and evaporated under reduced pressure. The residue was triturated with ethanol and filtered to afford 5chloro-2-phenyl-1,2,4-triazolo[4,3-]quinazolin-3-one (1.8 g) as a yellow solid. m.p. 167–168° C.

EXAMPLE III

Compound 1

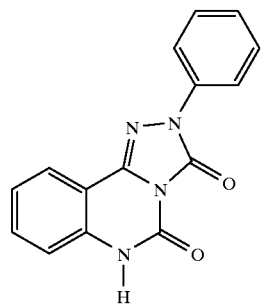

A mixture of 5-chloro-2-phenyl-1,2,4-triazolo[4,3-c] quinazolin-3-one (1g, 3.4 mmol) and sodium bicarbonate (500 mg, 5.9 mmol) in dioxane/$H_2O$ (5:1, 200 ml) was heated at 60° C. for 1.5 hours. The reaction mixture was poured into water and extracted with ethyl acetate (3×100 ml). The combined organic layers were washed with water followed by brine, dried over $Na_2SO_4$ and evaporated under reduced pressure. The residue was recrystallized from ethanol to afford 2-phenyl-5,6-dihydro-5-oxo-[6H]- 1,2,4-triazolo[4,3-c]quinazolin-3-one (Compound 1) as a white solid. m.p. 342–343° C.

EXAMPLE IV

Compound 2

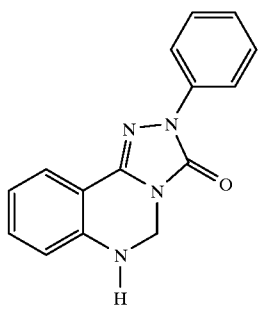

A mixture of 5-chloro-2-phenyl-1,2,4triazolo[4,3-c]-quinazolin-3-one (1g, 3.4 mmol), N,N-diisopropylethylamine (1 ml, 6.7 mmol) and 10% Pd-C (200 mg) in ethanol was shaken under hydrogen at 50 psi overnight. The reaction was diluted with $CHCl_3$ and filtered through Celite. The filtrate was evaporated under reduced pressure and the residue dissolved in dichloromethane. The solution was washed with water, dried over $Na_2SO_4$ and evaporated under reduced pressure to yield 2-phenyl-5,6-dihydro-1,2,4-triazolo[4,3-c]quinazolin-3-one (Compound 2) as a white solid. m.p. 202–204° C.

EXAMPLE V

The following compounds are prepared essentially according to the procedures described in Examples I–IV:

(a) 2-(4-Chlorophenyl)-5,6dihydro-5-oxo-[6H]-1,2,4-triazolo[4,3-c]-quinazolin-3-one (Compound 3), m.p. >360° C.
(b) 2-(4-Methylphenyl)-5,6 dihydro-5-oxo-[6H]-1,2,4-triazolo[4,3-c]-quinazolin-3-one (Compound 4), m.p. >350° C.
(c) 2-(2-Pyridyl)-5,6-dihydro5-oxo-[6H]-1,2,4-triazolo[4,3-c]quinazolin-3-one (Compound 5), m.p. 320–321° C.
(d) 2-(3-Fluorophenyl)-5,6dihydro-5-oxo-[6H]-1,2,4-triazolo[4,3-c]-quinazolin-3-one (Compound 6), m.p. 325–328° C.
(e) 2-(4-Methoxyphenyl)-5,6-dihydro-5-oxo-[6H]-1,2,4-triazolo[4,3-c]-quinazolin-3-one (Compound 7), m.p. 341–342° C.
(f) 2-(2-Fluorophenyl)-5,6-dihydro5-oxo-[6H]-1,2,4-triazolo[4,3-c]-quinazolin-3-one (Compound 8), m.p. >320° C.
(g) 2-(4-Ethoxycarbonylphenyl)-5,6-dihydro-5-oxo-[6H]-1,2,4-triazolo[4,3-c]quinazolin-3-one (Compound 9), m.p. 303–305° C.
(h) 2-(3-Fluorophenyl)-5,6dihydro 1,2,4-triazolo[4,3-c]quinazolin-3-one (Compound 10), m.p. 226–228° C.
(i) 2-(4-Methoxyphenyl)-5,6-dihydro-1,2,4-triazolo[4,3-c]quinazolin-3-one (Compound 11), m.p. 145–146° C.
(j) 2-(4Methylphenyl-5,6-dihydro-1,2,4-triazolo[4,3-c]quinazolin-3-one (Compound 12), m.p. 194–195° C.
(k) 2-(2-Pyridyl)-5,6-dihydro-1,2,4-triazolo[4,3-c]quinazolin-3-one (Compound 13), m.p. 251–253° C.
(l) 2-(2-Fluorophenyl)-5,6-dihydro-1,2,4-triazolo[4,3-c]quinazolin-3-one (Compound 14), m.p. 231–233° C.
(m) 2-(4-Fluorophenyl)-5,6-dihydro-1,2,4-tniazolo[4,3-c]quinazolin-3-one (Compound 15), m.p. 168–170° C.
(n) 2-(2,5-Difluorophenyl)-5,6-dihydro-1,2,4-triazolo[4,3-c]quinazolin-3-one (Compound 16), m.p. 161–162° C.
(o) 2-(2,4-Difluorophenyl)-5,6dihydro-1,2,4-triazolo[4,3-c]quinazolin-3-one (Compound 17), m.p. 230–232° C.
(p) 2-[4-(Ethoxycarbonyl)phenyl]-5,6dihydro-1,2,4-triazolo-[4,3-c]-quinazolin-3-one (Compound 18), m.p. 161–163° C.

EXAMPLE VI

Compound 19

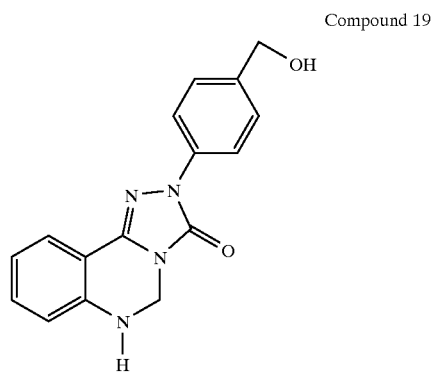

2-[4-(Ethoxycarbonyl)phenyl]-5,6dihydro-1,2,4-triazolo-[4,3-c]-quinazolin-3-one (Compound 18) (1 g, 3.0 mmol) was mixed with THF at 0° C. DIBAL (1.5M in Toluene, 4.6 ml) was added to the reaction dropwise and stirred for 10 min. at 0° C. The reaction was quenched with 10% NaOH solution and extracted with $CH_2Cl_2$ (3×100 ml). The combined organic layers were dried over $Na_2SO_4$ and evaporated under reduced pressure to afford 2-[4-(hydroxymethyl)-phenyl]-5,6dihydro-1,2,4-triazolo[4,3-c]-quinazolin-3-one (Compound 19), m.p. 152–154° C.

EXAMPLE VII

Compound 20

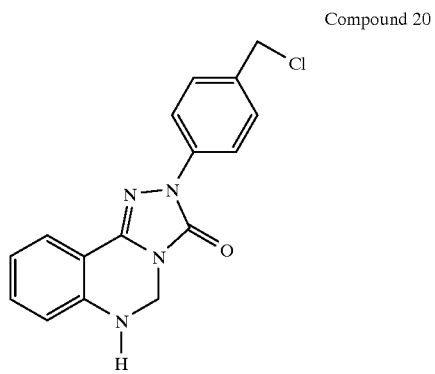

A mixture of 2-[4-(hydroxymethyl)-phenyl]-5,6-dihydro-1,2,4-triazolo[4,3-c]-quinazolin-3-one (Compound 19) (500 mg, 1.6 mmol) and excess $SOCl_2$ was heated at 50° C for 1 hour. $SOCl_2$ was evaporated under reduced pressure and the residue was washed with ether to afford 2-[4-(chloromethyl)-phenyl]-5,6-dihydro-1,2,4-triazolo[4,3-c]-quinazolin-3-one (Compound 20).

EXAMPLE VII

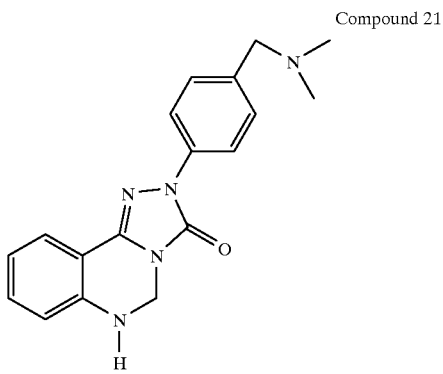

Compound 21

A mixture of 2-[4-(chloromethyl)-phenyl]-5,6-dihydro-1,2,4-triazolo[4,3-c]-quinazolin-3-one (Compound 20) (150 mg, 0.48 mmol) and dimethylamine (1 ml, 40% in H₂O) in THF was heated at 40° C. for 1.5 hours. The reaction was extracted with CH₂Cl₂ (3×50 ml) and the combined organic layers were dried over Na₂SO₄ and evaporated under reduced pressure. The residue was dissolved in ethyl acetate and saturated HCl/ethyl acetate solution was added to yield 2-[4-(N,N-dimethylaminomethyl)phenyl]-5,6-dihydro-1,2,4-triazolo-[4,3-c]quinazolin-3-one hydrochloride (Compound 21), m.p. 244–247° C.

EXAMPLE IX

The following compounds are prepared essentially according to the procedures described in Examples VI–VIII:

(a) 2-[4-(Hydroxymethyl)phenyl]-5,6-dihydro-5-oxo-6[H]-1,2,4-triazolo[4,3-c]-quinazolin-3-one (Compound 22), m.p. 316–317° C.
(b) 2-[4-(Chloromethyl)phenyl]-5,6-dihydro-5-oxo-6[H]-1,2,4-triazolo[4,3-c]-quinazolin-3-one (Compound 23), m.p. 308–310° C.
(c) 2-[4-(Aminomethyl)phenyl]-5,6dihydro-1,2,4-triazolo[4,3-c]quinazolin-3-one (Compound 24), m.p. 118 ° C. dec.
(d) 2-[4(N-Methylaminomethyl)phenyl]-5,6-dihydro-1,2,4-triazolo[4,3-c]-quinazolin-3-one hydrochloride (Compound 25), m.p. >85° C.
(e) 2-[4-(Ethylaminomethyl)phenyl]-5,6dihydro-1,2,4-triazolo[4,3-c]-quinazolin-3-one hydrochloride (Compound 26), m.p. >140° C.

EXAMPLE X

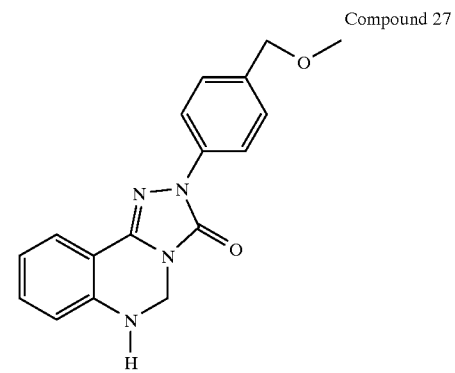

Compound 27

To the solution of 2-[4-(chloromethyl)phenyl]-5,6-dihydro-1,2,4-triazolo[4,3-c]quinazolin-3-one (Compound 20) (150 mg, 0.48 mmol) and methanol (30 ml) was added NaOMe (500 ml, 20% in MeOH) dropwise and stirred for 1 hour. The reaction was quenched with water and extracted with CH₂Cl₂ (3×50 ml). The combined organic layers were dried over Na₂SO₄ and evaporated under reduced pressure. The residue was purified by preparative TLC plate (1000 micron) (50% ethyl acetate/hexane) to afford 2-[4(-methoxymethyl)phenyl]]-5,6-dihydro-1,2,4-triazolo-[4,3-c]-quinazolin-3-one (Compound 27), m.p. 162–164° C.

EXAMPLE XI

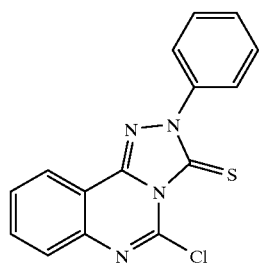

To a mixture of 2-chloro-4-phenylhydraziuinazoline (example I) (600 mg, 2.2 mmol) and triethylamine (800 ml, 5.7 mmol) in THF (50 ml) was added thiophosgene (180 ml, 2.3 mmol) slowly and stirred for additional 5 min. The reaction mixture was poured into water and extracted with CH₂Cl₂ (3×50ml). The combined organic layers were dried over Na₂SO₄ and evaporated under reduced pressure. The residue was triturated with ethanol and the precipitate was filtered to afford 5chloro2-phenyl-1,2,4triazolo[4,3c]quinazolin-3-thione.

EXAMPLE XII

Compound 28

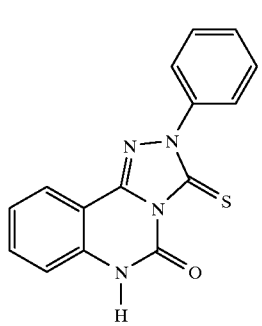

A mixture of 5-chloro-2-phenyl-1,2,4-triazolo[4,3-c]quinazolin-3-thione (200 mg, 0.64 mmol), NaHCO$_3$ (65 mg, 0.77 mmol) and H$_2$O (5 ml) in dioxane (80 ml) was heated at 50° C. for 1.5 hours. The reaction was poured into water (100 ml) and extracted with ethyl acetate (3×50 ml). The combined organic layers were washed with water, then brine, dried over Na$_2$SO$_4$ and evaporated under reduced pressure. The residue was purified by preparative TLC plate (1000 micron) (80% ethyl acetate/hexane) to afford 2-phenyl-5,6-dihydro-5-oxo-6[H]-1,2,4-triazolo[4,3-c]quinazolin-3-thione (compound 28), m.p. >300° C.

EXAMPLE XIII

Compound 29

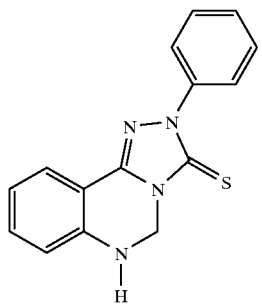

A mixture of 5-chloro-2-phenyl-1,2,4-triazolo[4,3-c]-quinazolin-3-thione (200 mg, 0.64 mmol) and zinc dust (10 mg, 150 mmol) in acetic acid (5 ml) was heated to reflux temperature. The reaction was filtered, neutralized with saturated NaHCO$_3$ solution and extracted with CH$_2$Cl$_2$ (3×50 ml). The combined organic layers were dried over Na$_2$SO$_4$ and evaporated under reduced pressure. The residue was washed with ethanol and filtered to afford 2-phenyl-5,6dihydro-1,2,4-triazolo[4,3-c]quinazolin-3-thione (compound 29), m.p. 222–223° C.

EXAMPLE XIV

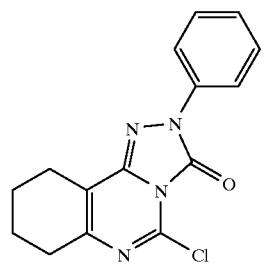

A mixture of 2,4-dichloro-5,6,7,8-tetrahydroquinazoline [prepared according to the procedure described by M. Botta et al., 40, *Tetrahedron*, (1984), 3313] (500 mg, 2.4 mmol), phenylhydrazine (270 mg, 2.5 mmol) and N,N-diisopropylethylamine (1 ml, 5.7 mmol) in THF (50 ml) was heated at reflux temperature overnight. The reaction was cooled to room temperature and phosgene (200 ml, 20% in toluene) was added slowly and stirred for an additional 10 min. The mixture was poured into water and extracted with ethyl acetate (3×50 ml). The combined organic layers were washed with brine, dried over Na$_2$SO$_4$ and evaporated under reduced pressure. The residue was triturated with ethanol and filtered to afford 5chloro-2-phenyl-7,8,9,10-tetrahydro-1,2,4-triazolo[4,3-c]quinazolin-3-one, m.p. 205–207° C.

EXAMPLE XV

Compound 30

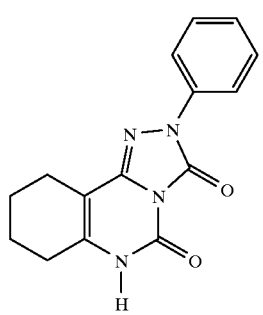

A mixture of 5-chloro-2-phenyl-7,8,9,10-tetrahydro-1,2,4-triazolo[4,3-c]quinazolin-3-one (150 mg, 0.5 mmol) and sodium bicarbonate (75 mg, 0.9 mmol) in dioxane/H$_2$O (5:1) (80 ml) was heated at 60° C. for 1.5 hours. The reaction mixture was poured into water and extracted with ethyl acetate (3×50 ml). The combined organic layers were washed with water then brine, dried over Na$_2$SO$_4$ and evaporated under reduced pressure. The residue was recrystallized from ethanol to afford 2-phenyl-5,6-dihydro-5-oxo-[6H]-7,8,9,10-tetrahydro-1,2,4-triazolo[4,3-c]-quinazolin-3-one (Compound 30) as a white solid. m.p. >320° C.

EXAMPLE XVI

Compound 31

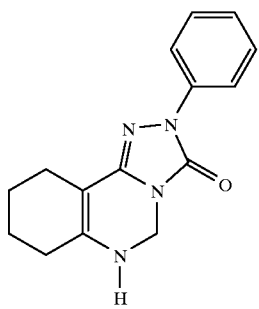

A mixture of 5-chloro-2-phenyl-7,8,9,10-tetrahydro-1,2,4-triazolo[4,3-c]quinazolin-3-one (150 mg, 0.5 mmol), diisopropylethylamine (130 ml, 0.74 mmol) and 10% Pd-C (30 mg) was hydrogenated under $H_2$ balloon for 1 hour. The reaction was filtered through Celite. $NaBH_4$ (30 mg, 0.79 mmol) was added to the filtrate and the mixture was heated to reflux temperature. The reaction was poured into water and extracted with $CH_2Cl_2$ (3×50 ml). The combined organic layers were dried over $Na_2SO_4$ and evaporated under reduced pressure. The residue was triturated with ethanol and filtered to afford 2-phenyl-5,6,7,8,9,10-hexahydro-1,2,4-triazolo[4,3-c]-quinazolin-3-one (Compound 31), m.p. 158–159° C.

EXAMPLE XVII

Compound 32

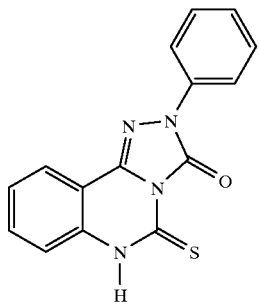

A mixture of 5-chloro-2-phenyl-1,2,4-triazolo[4,3-c]-quinazolin-3-one (120 mg, 0.4 mmol) and thiourea (40 mg, 0.52 mmol) in ethanol (20 ml) was stirred at room temperature overnight. The reaction was poured into water and extracted with $CH_2Cl_2$ (3×50 ml). The combined organic layers were washed with water then brine, dried over $Na_2SO_4$ then evaporated under reduced pressure. The residue was washed with ethanol and filtered to afford 2-phenyl-5,6-dihydro-5-thio-6[H]-1,2,4-triazolo[4,3-c]quinazolin-3-one as a solid (Compound 32), m.p. 342–344° C.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

We claim:
1. A compound of the formula:

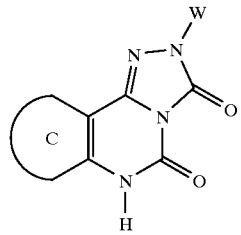

or the pharmaceutically acceptable salts thereof wherein

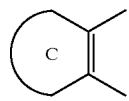

represents

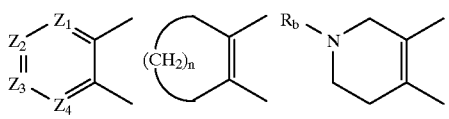

wherein:

$Z_1$, $Z_2$, $Z_3$, and $Z_4$ independently represent nitrogen or $CR_a$, where each $R_a$ independently is hydrogen, halogen, hydroxy, amino, or phenyl or pyridyl where phenyl and pyridyl are optionally substituted with halogen, alkyl, or alkoxy;

n is 1, 2 or 3; and $R_b$ is hydrogen, alkyl, phenyl, 2-, 3- or 4-pyridyl, phenylalkyl, or 2-, 3-, or 4-pyridylalkyl, where each phenyl or pyridyl ring is optionally substituted with up to two groups selected from halogen, hydroxy, alkyl, or alkoxy; and W is phenyl optionally substituted with up to five groups selected independently from halogen, cyano, hydroxy, straight or branched chain lower alkyl having 1–6 carbon atoms or cycloalkyl having 3–7 carbon atoms, amino, mono or dialkylamino where each alkyl is independently straight or branched chain lower alkyl having 1–6 carbon atoms or cycloalkyl having 3–7 carbon atoms, straight or branched chain lower alkoxy having 1–6 carbon atoms, cycloalkyl alkoxy having 3–7 carbon atoms, or $NR_1COR_2$, $COR_2$, $CONR_1R_2$ or $CO_2R_2$ where $R_1$ and $R_2$ are the same or different and represent hydrogen or straight or branched chain lower alkyl having 1–6 carbon atoms or cycloalkyl having 3–7 carbon atoms.

2. A compound according to claim 1, wherein W is phenyl substituted with a hydroxyalkyl group.

3. A compound according to claim 1, wherein W represents phenyl substituted in the para position with a hydroxyalkyl group.

4. A compound according to claim 1 which is 2-[4-(N,N-dimethylaminomethyl)phenyl]-5,6-dihydro-1,2,4-triazolo-[4,3-c]quinazolin-3-one.

5. A compound according to claim 1 which is 2-[4-(N-Methylaminomethyl)phenyl]-5,6-dihydro-1,2,4-triazolo[4,3-c]-quinazolin-3-one.

6. A compound according to claim 1 which is 2-[4-(Ethylaminomethyl)phenyl]-5,6-dihydro-1,2,4-triazolo[4,3-c]-quinazolin-3-one.

7. A compound of the formula:

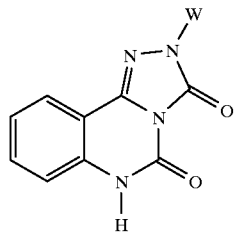

or the pharmaceutically acceptable salts thereof where W is phenyl optionally substituted with up to five groups selected independently from halogen, cyano, hydroxy, straight or branched chain lower alkyl having 1–6 carbon atoms or cycloalkyl having 3–7 carbon atoms, amino, mono or dialkylamino where each alkyl is independently straight or branched chain lower alkyl having 1–6 carbon atoms or cycloalkyl having 3–7 carbon atoms, straight or branched chain lower alkoxy having 1–6 carbon atoms, cycloalkyl alkoxy having 3–7 carbon atoms, or $NR_1COR_2$, $COR_2$, $CONR_1R_2$ or $CO_2R_2$ where $R_1$ and $R_2$ are the same or different and represent hydrogen or straight or branched chain lower alkyl having 1–6 carbon atoms or cycloalkyl having 3–7 carbon atoms.

8. A compound of the formula:

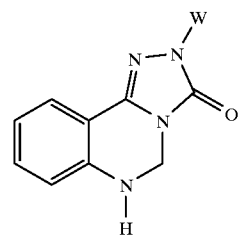

or the pharmaceutically acceptable salts thereof wherein W is phenyl optionally substituted with up to five groups selected independently from halogen, cyano, hydroxy, straight or branched chain lower alkyl having 1–6 carbon atoms or cycloalkyl having 3–7 carbon atoms, amino, mono or dialkylamino where each alkyl is independently straight or branched chain lower alkyl having 1–6 carbon atoms or cycloalkyl having 3–7 carbon atoms, straight or branched chain lower alkoxy having 1–6 carbon atoms, cycloalkyl alkoxy having 3–7 carbon atoms, or $NR_1COR_2$, $COR_2$, $CONR_1R_2$ or $CO_2R_2$ where $R_1$ and $R_2$ are the same or different and represent hydrogen or straight or branched chain lower alkyl having 1–6 carbon atoms or cycloalkyl having 3–7 carbon atoms.

9. A compound according to claim 8, wherein W represents phenyl mono or disubstituted with halogen, hydroxyalkyl, or alkylaminoalkyl.

10. A compound according to claim 8, wherein W represents phenyl disubstituted with halogen, or phenyl monosubstituted with hydroxyalkyl, or alkylaminoalkyl.

11. A compound according to claim 8, wherein W represents phenyl ortho and para substituted with fluoro.

12. A compound according to claim 8, wherein W represents phenyl para substituted with hydroxymethyl or methylaminomethyl.

* * * * *